(12) United States Patent
Kim et al.

(10) Patent No.: US 10,792,238 B2
(45) Date of Patent: Oct. 6, 2020

(54) COSMETIC COMPOSITION HAVING HIGH DOSAGE FORM STABILITY

(71) Applicant: AMOREPACIFIC CORPORATION, Seoul (KR)

(72) Inventors: Yu Jung Kim, Yongin-si (KR); Hyeon Chung Kim, Yongin-si (KR); Jae Won Yoo, Yongin-si (KR); Yong Jin Kim, Yongin-si (KR); Do Hoon Kim, Yongin-si (KR); Sung Il Park, Yongin-si (KR)

(73) Assignee: AMOREPACIFIC CORPORATION, Seoul (KR)

( * ) Notice: Subject to any disclaimer, the term of this patent is extended or adjusted under 35 U.S.C. 154(b) by 0 days.

(21) Appl. No.: 16/290,210

(22) Filed: Mar. 1, 2019

(65) Prior Publication Data

US 2019/0192412 A1    Jun. 27, 2019

Related U.S. Application Data

(63) Continuation of application No. 15/739,000, filed as application No. PCT/KR2016/005220 on May 18, 2016, now abandoned.

(30) Foreign Application Priority Data

Jun. 30, 2015 (KR) .................. KR10-2015-0092713
May 17, 2016 (KR) .................. KR10-2016-0060155

(51) Int. Cl.
| | |
|---|---|
| C07H 15/04 | (2006.01) |
| A61K 8/60 | (2006.01) |
| A61Q 19/08 | (2006.01) |
| A61K 8/49 | (2006.01) |
| A61K 8/06 | (2006.01) |
| A61Q 19/02 | (2006.01) |

(52) U.S. Cl.
CPC ............. *A61K 8/602* (2013.01); *A61K 8/06* (2013.01); *A61K 8/4973* (2013.01); *A61Q 19/02* (2013.01); *A61Q 19/08* (2013.01); *A61K 2800/52* (2013.01)

(58) Field of Classification Search
CPC ........ A61K 8/602; A61K 8/06; A61K 8/4973; A61K 2800/52; A61Q 19/08; A61Q 19/02; C07H 15/04; C07H 15/06
USPC .............................................. 424/62; 536/4.1
See application file for complete search history.

(56) References Cited

U.S. PATENT DOCUMENTS

| | | | |
|---|---|---|---|
| 6,916,844 B2 | 7/2005 | Roh et al. | |
| 7,989,599 B2 | 8/2011 | Suzuki et al. | |
| 2003/0236299 A1 | 12/2003 | Roh et al. | |
| 2010/0004472 A1 | 1/2010 | Kitagawa et al. | |
| 2010/0168405 A1* | 7/2010 | Suzuki | A61K 8/60 |
| | | | 536/4.1 |
| 2010/0278784 A1 | 11/2010 | Pojasek et al. | |
| 2010/0298760 A1 | 11/2010 | Olle et al. | |
| 2011/0021397 A1* | 1/2011 | Holerca | A61K 8/35 |
| | | | 510/100 |
| 2012/0183592 A1 | 7/2012 | Kitagawa et al. | |

FOREIGN PATENT DOCUMENTS

| | | |
|---|---|---|
| JP | 2009-149566 A | 7/2009 |
| JP | 2009167159 A | 7/2009 |
| JP | 2009201478 A | 9/2009 |
| JP | 2009275017 A | 11/2009 |
| JP | 2010-018558 A | 1/2010 |
| JP | 2011502571 A | 1/2011 |
| JP | 2011-074058 A | 4/2011 |
| JP | 4675033 B2 | 4/2011 |
| JP | 2011105607 A | 6/2011 |
| JP | 4982822 B2 | 7/2012 |
| JP | 2014101294 A | 6/2014 |
| JP | 2014181208 A | 9/2014 |
| JP | 5693245 B2 | 4/2015 |
| JP | 5707062 B2 | 4/2015 |
| KR | 100482668 B1 | 4/2005 |
| KR | 100494535 B1 | 6/2005 |
| KR | 100704468 B1 | 4/2007 |
| KR | 20080072743 A | 8/2008 |
| KR | 20120091016 A | 8/2012 |
| KR | 20130025768 A | 3/2013 |
| KR | 20130026626 A | 3/2013 |

(Continued)

OTHER PUBLICATIONS

Savjani et al, Title: Drug Solubility: Importance and Enhancement Techniques, International Scholarly Research Network, vol. 2012, pp. 1-10, published Jul. 5, 2012). (Year: 2012).*
Modi et al, title: A comparative solubility enhancement profile of valdecoxib with different solubilization approaches; Indian J Pharm Sci, 2007, 69 (2): 274-278. (Year: 2007).*
Yoon et al., "Multilamellar Liquid Crystals for the Stabilization of Retinoids", J. Kor. Pharrn. Sci., 1999, vol. 29, No. 4, pp. 279-285.
Kim et al., "The effects of a novel synthetic retinoid, seletinoid G, on the expression of extracellular matrix proteins in aged human skin in vivo", Clinica Chimica Acta, 2005, vol. 362, pp. 161-169.
Kim et al., "Nanoemulsification of pseudo-ceramide by molecular association with mannosylerythritol lipid", Colloids and Surfaces B: Biointerfaces, 2014, vol. 116, pp. 597-602.
Sajna et al., "Studies on biosurfactants from *Pseudozyrna* sp. NII 08165 and their potential application as laundry detergent additives", Biochemical Engineering Journal, 2013, vol. 78, pp. 85-92.

(Continued)

*Primary Examiner* — Yanzhi Zhang
(74) *Attorney, Agent, or Firm* — Lucas & Mercanti, LLP

(57) ABSTRACT

The present invention relates to a cosmetic composition using a mannosylerythritol lipid, which is a kind of glycolipid, as a stabilizer in order to prevent kojyl methylenedioxycinnamate, which is an active ingredient having various skin effects such as antiaging, whitening and antioxidation, from causing crystallization inside a dosage form. Even if the cosmetic composition according to the present invention contains a high concentration of an active ingredient, crystal precipitation does not occur in various dosage forms, and thus the functionality of the active ingredient is maximized, skin delivery is increased and the texture during use is improved.

3 Claims, 1 Drawing Sheet

(56) References Cited

FOREIGN PATENT DOCUMENTS

KR    20150062895 A    6/2015

OTHER PUBLICATIONS

Rho et al., "Kojyl cinnamate ester derivatives promote adiponectin production during adipogenesis in human adipose tissue-derived mesenchymal stem cells", Biooraanic & Medicinal Chemistry Letters, 2014, vol. 24, No. 9, pp. 2141-2145.

Cho et al., "Depigmenting activity of new kojic acid derivative obtained as a side product in the synthesis of cinnamate of kojic acid", Biooraanic & Medicinal Chemistry Letters, 2012, vol. 22, No. 5, pp. 2004-2007.

Rho et al., "New 5-Hydroxy-2-(hydroxymethyl)-4H-pyran-4-one Derivative Has Both Tyrosinase Inhibitory and Antioxidant Properties", Bull. Korean Chem. Soc., 2007, vol. 28, No. 3, pp. 471-473.

Rho et al., "Ester Derivatives of Kojic Acid arid Polyphenols Containing Adarnantane Moiety with Tyrosinase Inhibitory and Anti-inflammatory Properties", Bull. Korean Chem. Soc., 2011, vol. 32, No. 4, pp. 1411-1414.

Kim et al., "Extracellular production of a glycolipid biosurfactant, mannosylerythritol lipid, from Candida antarctica", Biotechnology Letters, 2002, vol. 24, pp. 225-229.

Kim et al., "Characterization of a biosurfactant, mannosylerythritol lipid produced from *Candida* sp. SY16", Appl Microbiol Biotechnol, 1999, vol. 52, pp. 713-721.

Kim et al., "Fabrication of pseudo-ceramide-based lipid rnicroparticles for recovery of skin barrier function", Colloids and Surfaces B: Biointerfaces, 2012, vol. 94, pp. 236-241.

International Search Report for International Application No. PCT/KR2016/005220. (3 Pages) (dated Aug. 25, 2016).

* cited by examiner

[Figure 1]
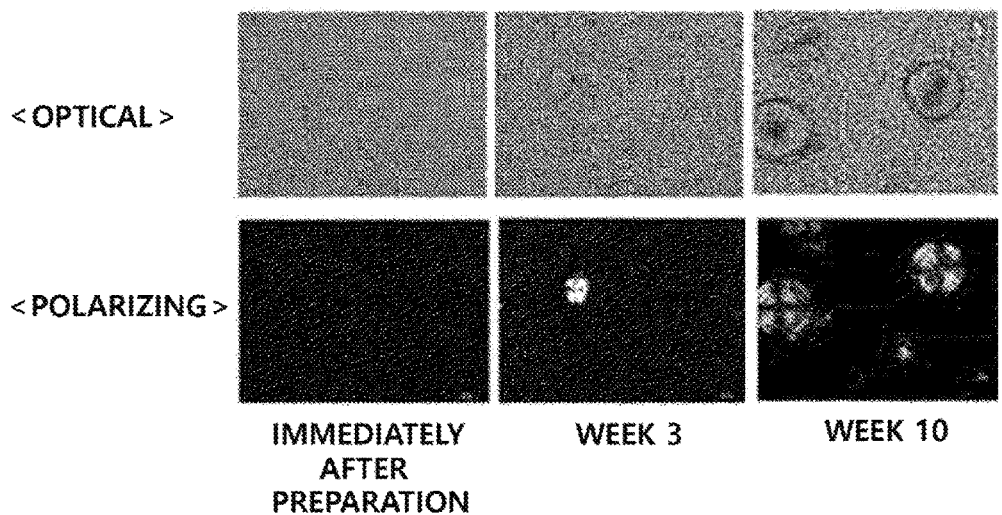
| | IMMEDIATELY AFTER PREPARATION | WEEK 3 | WEEK 10 |
[Figure 2]
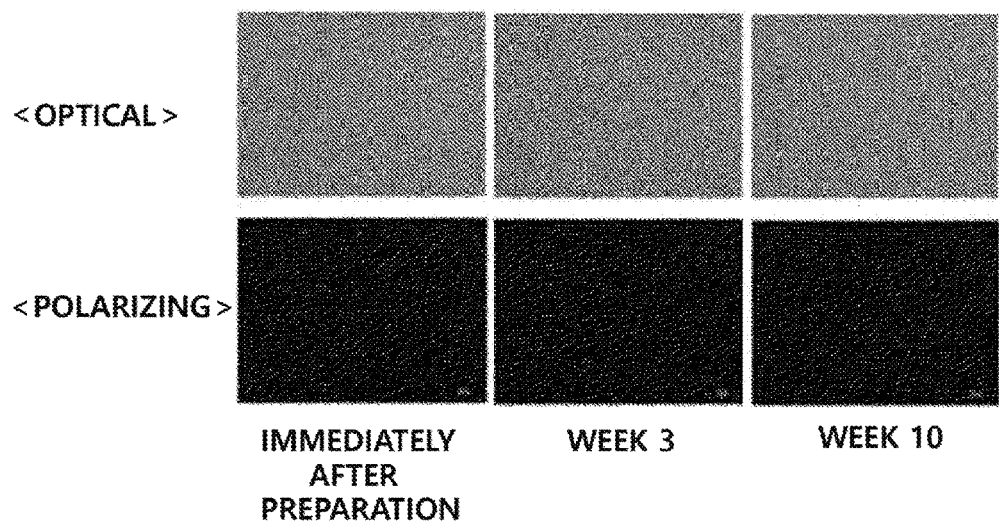

COSMETIC COMPOSITION HAVING HIGH DOSAGE FORM STABILITY

CROSS-REFERENCE TO RELATED APPLICATIONS

This application is a continuation of U.S. application Ser. No. 15/739,000, filed Dec. 21, 2017 which in turn is a 371 of PCT/KR2016/005220, filed May 18, 2016 which claims the benefit of Korean Patent Application No. 10-2015-0092713, filed Jun. 30, 2015 and Korean Patent Application No. 10-2016-0060155, filed May 17, 2016 the contents of each of which are incorporated herein by reference.

TECHNICAL FIELD

The present invention relates to a cosmetic composition in which a mannosylerythritol lipid is used as a stabilizer to enhance the dosage form stability of a composition including kojyl methylenedioxycinnamate used as an active ingredient for cosmetics.

BACKGROUND ART

A cosmetic composition includes various active ingredients to exhibit certain effects. Particularly, the skin is easily damaged by external stimuli because the skin is directly exposed to external environments.

Therefore, a number of materials have been known to prevent damage to the skin and impart various effects. For example, kojyl methylenedioxycinnamate (Trade Name: Seletinoid G™) is one of such materials, and particularly has excellent effects such as antiaging, antioxidant, and whitening effects.

However, the kojyl methylenedioxycinnamate is not easily dissolved in a composition due to strong crystallinity, and recrystallized or precipitated in a very short time even after dissolved in the composition, resulting in degraded skin absorption or texture in use of products. In effect, these problems make it difficult to use the kojyl methylenedioxycinnamate as an active ingredient of a cosmetic composition even when the kojyl methylenedioxycinnamate has excellent effects.

There have been various attempts conducted to solve such problems such as poor solubility of the kojyl methylenedioxycinnamate.

For example, as a method widely used to dissolve a crystalline material, there is a method using a microcapsule formed of a polymer. Also, there is an attempt to enhance solubility of kojyl methylenedioxycinnamate by dissolving the kojyl methylenedioxycinnamate and another highly crystalline material in a polar oil (Korean Patent Publication No. 10-2015-0062895).

However, the former has problems in that the solubility of the active ingredient inside a capsule is determined depending on the compatibility between polymers or the crystallinity of the polymers themselves, and a release rate of the active ingredient becomes very slow because crystals are independently formed in a polymer capsule in most cases, resulting in degraded efficiency in provision of the active ingredient.

Also, the latter still has a limitation in being commercialized because it is cumbersome and uneconomical and has no remarkable effect of improving solubility.

Therefore, there is a demand for development of more effective methods to lower the crystallinity of kojyl methylenedioxycinnamate and maintain the stability in a composition.

PRIOR ART DOCUMENT

Korean Patent Publication No. 2015-0062895 entitled "Cosmetic Compositions Containing Two Kinds of Compounds Comprising Phenyl Rings"

DISCLOSURE

Technical Problem

To solve the above problems, the present inventors have selected various stabilizers and screened the stabilizers to select the best stabilizer capable of inhibiting crystallization of kojyl methylenedioxycinnamate, and found that crystal precipitation does not occur for a long time when it is determined whether crystals are generated after the stabilizer is prepared into a dosage form.

Therefore, it is an object of the present invention to provide a cosmetic composition including kojyl methylenedioxycinnamate and a stabilizer.

Technical Solution

To solve the above problems, according to an aspect of the present invention, there is provided a cosmetic composition, which includes:

kojyl methylenedioxycinnamate represented by the following Formula 1 as an active ingredient; and a mannosylerythritol lipid (MEL) represented by the following Formula 2 as a stabilizer:

[Formula 1]

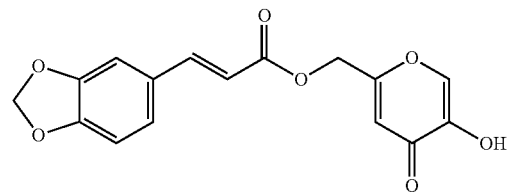

[Formula 2]

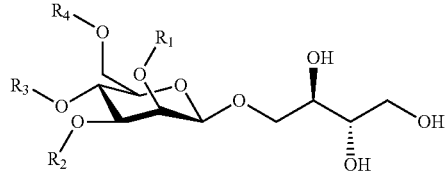

wherein $R_1$ to $R_4$ are as described in this specification.

In this case, the kojyl methylenedioxycinnamate may be included at a content of 0.05 to 0.25% by weight, based the total weight of the cosmetic composition.

Also, the mannosylerythritol lipid may be included at a content of 0.25 to 5.0% by weight, based the total weight of the cosmetic composition.

Particularly, the kojyl methylenedioxycinnamate and the mannosylerythritol lipid may be included at a weight ratio of greater than 1:2.5 to 1:100.

Advantageous Effects

The cosmetic composition according to the present invention serves to enhance stability of a dosage form including kojyl methylenedioxycinnamate, and thus can be useful in improving quality of products because problems regarding precipitation of crystals in conventional dosage forms are solved to prevent a decrease in texture in use caused due to a feeling of irritation by foreign substances when the crystals precipitate.

Because a high concentration of the kojyl methylenedioxycinnamate having antiaging, antioxidant and whitening effects may be included in the cosmetic composition due to such increased dosage form stability, the function of the kojyl methylenedioxycinnamate can be maximized to enhance skin whitening and skin elasticity and inhibit formation of wrinkles, thereby preventing skin ageing.

DESCRIPTION OF DRAWINGS

FIG. 1 is an image of a cosmetic composition prepared in Comparative Example 1 taken with time using an optical microscope (×500) and a polarizing microscope (×500).

FIG. 2 is an image of a cosmetic composition prepared in Example 1 taken with time using an optical microscope (×500) and a polarizing microscope (×500).

BEST MODE

In the present invention, a novel cosmetic composition capable of fundamentally blocking crystal formation and precipitation from occurring in the cosmetic composition including kojyl methylenedioxycinnamate as an active ingredient.

Kojyl methylenedioxycinnamate is represented by the following Formula 1:

[Formula 1]

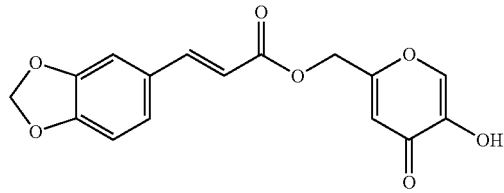

The kojyl methylenedioxycinnamate of Formula 1 is named 2-((3E)-4(2H,3H-benzo[3,4-d]-1,3-dioxolan-5-yl)-2-oxo-but-3-enyloxy)-5-hydroxy-4H-pyran-4-one according to the IUPAC system, and commercially sold on the market as the trade name 'Seletinoid G™'.

The kojyl methylenedioxycinnamate has various skin effects such as antiaging, whitening, and antioxidant effects, and has been used as an active ingredient of the cosmetic composition in various dosage forms. However, because such a compound is not easily dissolved in the composition due to strong crystallinity and problems such as crystallization and crystal precipitation may be caused with time even after the compound is dissolved in the composition, the dosage form stabilization may be seriously degraded, and the texture in use may be lowered.

Accordingly, as a kind of a glycolipid in which fatty acids are bound to sugars, a mannosylerythritol lipid (hereinafter referred to as 'MEL') is used as a stabilizer in the present invention to prevent crystallization of the compound.

The MEL is represented by the following Formula 2:

[Formula 2]

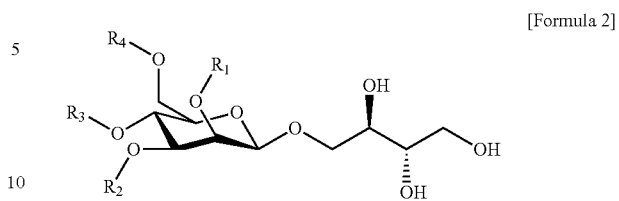

wherein $R_1$ and $R_2$ are the same or different from each other, and each independently a C2 to C24 aliphatic acyl group, and $R_3$ and $R_4$ are the same or different from each other, and each independently an acetyl group or hydrogen.

More preferably, $R_1$ and $R_2$ may be the same or different from each other, and each independently a C6 to C18 aliphatic acyl group, wherein the aliphatic acyl group is represented by $-C(=O)-(CH_2)_n-CH_3$. In this case, n may be in a range of 3 to 15.

The MEL may be any one selected from MEL-A, MEL-B, MEL-C, and MEL-D, which are defined by the following Formula 3:

[Formula 3]

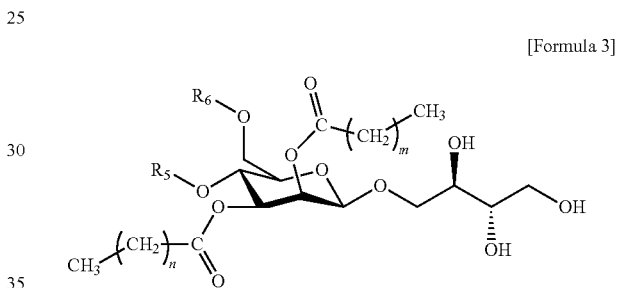

wherein $R_5$ and $R_6$ are the same or different from each other, and are an acetyl group or hydrogen, and n or m is an integer ranging from 6 to 10.

Preferably, the MEL-A is a compound in which $R_5$ and $R_6$ are an acetyl group in Formula, the MEL-B is a compound in which $R_5$ is hydrogen and $R_6$ is an acetyl group, the MEL-C is a compound in which $R_5$ is an acetyl group and $R_6$ is a hydrogen, and the MEL-D is a compound in which both $R_5$ and $R_6$ are hydrogen.

The MEL is one of biosurfactants having a surface activity.

A biosurfactant may be prepared from microorganisms. Therefore, the biosurfactant has a skin-protecting effect because the biosurfactant is high biodegradable, has low toxicity, is not harmful to the human body skin, and has an excellent moisturizing ability. Also, the biosurfactant is a material that has a degree of surface activity corresponding to those of chemically synthetic surfactants used in the related art because the biosurfactant has a minimum surface tension of 29 dyne/cm and a critical micelle concentration (CMC) of 15 μM (10 mg/L).

Preparation of the MEL is not particularly limited in the present invention, and may be performed as known in the related art. As one example, the MEL may be obtained from one or more corresponding microbes selected from *Candida* sp., *Torulopsis* sp., *Pseudomonas* sp., *Bacillus* sp., *Alcaligenes* sp., *Acinetobacter* sp., *Ustilago* sp., *Rhodococcus* sp., and the like.

In the present invention, when the MEL of Formula 2 is used as the stabilizer together with the kojyl methylenedioxycinnamate of Formula 1, the crystallization and crystal precipitation caused due to low dosage form stability of the kojyl methylenedioxycinnamate may be prevented. Such dosage form stability exhibits the same results even at low, room and high temperatures.

Various candidate materials known in the related art, such as a stabilizer, a surfactant, an emulsifying agent, a dispersing agent, and the like, may be used to enhance the dosage form stability, but should be selected in consideration of the chemical structure of the active ingredient. In this case, the same effect may be secured from all stabilizers. In preferred Experimental Example 1 of the present invention, each of MEL, ethyl alcohol, polysorbate 20, diethoxyethyl succinate and glyceryl/polyglyceryl-6-isostearate/behenate ester was used together with the kojyl methylenedioxycinnamate to prepare a dosage form, and the crystallization tendency of such components was checked. As a result, it was confirmed that no crystallization occurred with time only in the composition including the MEL, but the crystallization occurred seriously when the other components were used.

Also, the crystallization tendency according to the temperature was checked in Experimental Example 2. As a result, the composition exhibited excellent dosage form stability at all low, room and high temperatures when the MEL was added, and the crystallization occurred seriously when the MEL was not added. In this case, the crystallization tended to be further accelerated at a low temperature.

When crystals are formed in the dosage form through the crystallization, the active ingredient is not easily delivered to the skin, thereby reducing the effect of the active ingredient and causing a drop in product quality due to a feeling of irritation by foreign substances when in use. Therefore, it is very important to prevent these problems. Eventually, such problems may also be solved through the use of MEL in the present invention.

In addition, the MEL has an advantage in that kojyl methylenedioxycinnamate is included as the active ingredient at a high concentration of up to 0.25% by weight when the MEL is used to enhance the dosage form stability.

Meanwhile, the crystallization refers to the stability of a dosage form. For the purpose, the content of the active ingredient, the content of the MEL, and the content ratios of the active ingredient and MEL may be important parameters associated with the stability.

Preferably, the cosmetic composition of the present invention includes the kojyl methylenedioxycinnamate at 0.05 to 0.25% by weight, preferably 0.05 to 0.15% by weight, based on the total weight of the cosmetic composition. When the content of the kojyl methylenedioxycinnamate is less than this content range, effects obtained through the use of the kojyl methylenedioxycinnamate, that is, antiaging, whitening and antioxidant effects may not be secured. On the other hand, when the content of the kojyl methylenedioxycinnamate is greater than this content range, the crystallization may occur due to degraded stability.

Also, the MEL is used at content of 0.25 to 5.0% by weight, preferably 0.25 to 2.0% by weight, based on the total weight of the cosmetic composition. When the content of the MEL is less than this content range, stabilization of the kojyl methylenedioxycinnamate may not be achieved, which leads to crystallization. On the other hand, when the content of the MEL is greater than this content range, it is uneconomical because there is no difference in effects. Therefore, the MEL is properly used within this content range.

Particularly, as one of the parameters important in preventing the crystallization, the weight ratio of the MEL to the kojyl methylenedioxycinnamate may be possibly greater than 1:2.5. Preferably, the kojyl methylenedioxycinnamate and the MEL are used at a weight ratio of greater than 1:2.5 to 1:100, more preferably a weight ratio of 1:3 to 1:20. According to preferred Experimental Example 2 of the present invention, it is checked whether the crystallization occurs according to the content ratios. As a result, it is confirmed that crystals are formed when the kojyl methylenedioxycinnamate and MEL are used at a weight ratio of 1:2.5 or less, but the crystallization does not occur when the kojyl methylenedioxycinnamate and MEL are used at a weight ratio of greater than 1:2.5.

In this way, the cosmetic composition including the kojyl methylenedioxycinnamate and the MEL provides antiaging, whitening and antioxidant effects when applied onto the skin, thereby preventing skin aging through enhancing skin whitening and skin elasticity and inhibiting wrinkle formation.

The cosmetic composition according to the present invention may include a cosmetologically or dermatologically acceptable medium or base material so that it can be prepared into dosage forms. In addition to the components as the active ingredients, components included in the cosmetic composition of the present invention components generally used in the cosmetic composition. For example, the components may include an oily component, a moisturizing agent, a softening agent, a surfactant, an organic and inorganic pigment, an organic powder, a UV absorbent, a preservative, an antifoaming agent, a thickening agent, a disinfectant, an antioxidant, a plant extract, a pH control agent, an alcohol, a coloring agent, a flavoring agent, a blood flow stimulant, a cooling agent, an antihidrotic agent, and the like.

The cosmetic composition of the present invention may also be prepared into any dosage forms generally prepared in the related art. For example, the cosmetic composition may be prepared into dosage forms such as a solution, a suspension, an emulsion, a paste, a gel, a cream, a lotion, a powder, a soap, a surfactant-containing cleansing cream, an oil, a powder foundation, an emulsion foundation, a wax foundation, and a spray, but the present invention is not limited thereto. More specifically, the cosmetic composition may be prepared into dosage forms such as an emulsifying toner, a nourishing toner, a nourishing cream, a massage cream, an essence, an eye cream, a cleansing cream, a cleansing foam, a cleansing water, a pack, a spray, and a powder.

When the dosage form of the present invention is a paste, a cream, or a gel, an animal oil, a vegetable oil, wax, paraffin, starch, tragacanth, a cellulose derivative, polyethylene glycol, silicon, bentonite, silica, talc, or zinc oxide may be used as the carrier component.

When the dosage form of the present invention is a powder or a spray, lactose, talc, silica, aluminum hydroxide, calcium silicate, or polyamide powder may be used as the carrier component. Particularly in the case of sprays, the cosmetic composition may further include a propellant such as chlorofluorohydrocarbon, propane, butane, or dimethyl ether.

When the dosage form of the present invention is a solution or an emulsion, a solvent, a solubilizing agent, or an emulsifying agent may be used as the carrier component. For example, the carrier component may include water, ethanol, isopropanol, ethyl carbonate, ethyl acetate, glycerin, carbomer, benzyl alcohol, benzyl benzoate, propylene glycol, 1,3-butylene glycol, glycerol aliphatic ester, caprylic/capric triglycerides, hydrogenated polydecene, cetearyl glucoside, sorbitan stearate, polyethylene glycol, cetearyl alcohol, and the like.

When the dosage form of the present invention is a suspension, a liquid diluent such as water, ethanol or propylene glycol, a suspending agent such as ethoxylated isostearyl alcohol, polyoxyethylene sorbitol ester and polyoxyethylene sorbitan ester, microcrystalline cellulose, aluminum metahydroxide, bentonite, agar, or tragacanth may be used as the carrier component.

When the dosage form of the present invention is a surfactant-containing cleansing cream, fatty alcohol sulfate, aliphatic alcohol ether sulfate, sulfosuccinate monoester, isethionate, an imidazolinium derivative, methyl taurate, sarcosinate, fatty acid amide ether sulfate, alkyl amido betaine, aliphatic alcohol, fatty acid glyceride, fatty acid diethanol amide, vegetable oil, a lanolin derivative, or ethoxylated glycerol fatty acid ester may be used as the carrier component.

For example, the cosmetic composition according to the present invention may be an emulsion, that is, an emulsified dosage form.

The emulsion is a dosage form system most typically used in the field of cosmetics, and refers to a system in which an oily phase and an aqueous phase are uniformly dispersed using an emulsification technique. Such an emulsion may be prepared into various forms, depending on the compositions having a continuous phase. For example, a water-in-oil (W/O), oil-in-water (O/W), water-in-oil-in-water (W/O/W), or oil-in-water-in-oil (O/W/O) emulsion is possible. In the present invention, the shapes of the emulsion are not particularly limited.

In this case, a polyol is used together with water in the aqueous phase, and an oil is used in the oily phase. The aforementioned various additives, stabilizers, surfactants, UV absorbents, and the like may be added to each phase.

The water used in the aqueous phase is distilled water. Preferably, deionized distilled water is used. In this case, the water is used as the balance so that the total weight of the composition satisfies 100% by weight.

The polyol used in the aqueous phase is used for the purpose of moisturizing, and has a refractive index ranging from 1.3 to 1.5. In this case, one selected from the group consisting of glycerin, propylene glycol, butylene glycol, glycerin, erythritol, xylitol, maltitol glycerin, sorbitol, polyglycerin, polyethylene glycol, pentanediol, isoprene glycol, and a combination thereof is used as the polyol. The polyol may be used at a content of 0.1 to 20.0% by weight, based on the total weight of the composition.

The oil used in the oily phase is not particularly limited in the present invention. For example, any oils may be used as long as they are generally used in the related art. Typically, one selected from the group consisting of a hydrocarbon-based oil including polydecene and paraffin oil; an ester-based synthetic oil including cetyl ethylhexanoate, glyceryl trioctanoate, octyldodecyl myristate, isopropyl palmitate, isopropyl myristate, octyl palmitate, and the like; a silicon oil including cyclomethicone, dimethicone, and the like; an animal oil; a vegetable oil including mango butter, shea butter, *Theobroma grandiflorum* seed butter, macadamia seed oil, and the like; an ethoxylated alkyl ester-based oil; cholesterol; cholesteryl sulfate; phytosphingosine; sphingoid lipid; a C10 to C40 fatty alcohol such as batyl alcohol, behenyl alcohol, cetostearyl alcohol, cetyl alcohol, stearyl alcohol, and the like; caprylic/capric triglyceride, ceramide, and mixtures thereof may be used as the oil.

Furthermore, at least one of the aqueous and oily phases may further include a thickening agent. Typically, sodium polyacrylate copolymers, carbomers, crosslinked or non-crosslinked acrylic polymers, particularly crosslinked poly-acrylic acids as a multivalent functional base, for example, the trade name "CARBOPOL" commercially available from Goodrich Corp., cellulose derivatives, for example, methyl cellulose, hydroxymethyl cellulose, hydroxyethyl cellulose, hydroxypropyl methyl cellulose, carboxymethyl cellulose, sodium salts of carboxymethyl cellulose, cetyl stearyl alcohol, a mixture of oxyethylenated cetyl stearyl alcohol containing 33 mol ethylene oxide, guar gum, xanthan gum, and a combination thereof may be used as the thickening agent. In this case, the thickening agent may be used at a content of 0.01 to 10.0% by weight, based on the total weight of the composition.

Furthermore, at least one of the aqueous and oily phases may further include a surfactant.

For example, sorbitan stearate, sorbitan laurate, sorbitan palmitate, glyceryl stearate, polyglyceryl stearate, polyoxyethylene stearyl ether, polyoxyethylene oleate, polyoxyethylene sorbitan stearate, polyoxyethylene sorbitan laurate, polyoxyethylene sorbitan oleate, polyoxyethylene sorbitol hexaoleate, a polyoxyethylene ether-based compound of natural oils such as polyoxyethylene-hydrogenated castor oil, and the like, or a polyoxyethylene ether-based compound of polyoxypropylenes such as Poloxamer 168, Poloxamer 407, and the like, sodium stearate, potassium stearate, sodium laurate, sodium lauryl sulfate, sodium laureth sulfate, ammonium laureth sulfate, potassium cetyl phosphate, PEG-100 dimethicone, polyethylene glycol monoisostearate, cetearyl olivate, sorbitan olivate, hydrogenated lecithin, arachidyl glucoside, cetearyl alcohol, cetearyl glucoside, polysorbate 80, and polysorbate 60 may be used as the surfactant. In this case, the surfactant may be used at a content of 10% by weight or less, based on the total weight of the composition.

In addition, additives as known in the related art, such as a water-/oil-soluble physiologically active component, a moisturizing agent, a preservative, a pH regulator, fatty acid, an emulsifying agent, an antioxidant, a sunscreen, a pigment, a dye, a flavoring agent, a stabilizer, and the like, may be additionally added, when necessary. In this case, the types and contents of the additives may be properly selected by a person having ordinary skill in the art.

An emulsion dosage form is prepared into various forms by preparing an aqueous phase including water as a continuous phase, preparing an oily phase including an oil as a continuous phase, and varying a mixing order of the aqueous and oily phases. Specifically, the aqueous phase is heated at 50 to 90° C., preferably 60 to 80° C., and the oily phase is heated at 50 to 80° C., preferably 65 to 75° C. so that the other components are sufficiently dissolved in the oil.

In this case, the stirring is performed at a rotary speed of 2,000 to 4,000 rpm, preferably 3,000 rpm for 3 to 10 minutes in a vacuum emulsifier tank using a homomixer.

The kojyl methylenedioxycinnamate and the MEL according to the present invention may be added to either the aqueous phase or oily phase, or may be added after an emulsion is finally prepared. In one exemplary embodiment of the present invention, the kojyl methylenedioxycinnamate and the MEL may be added after the aqueous phase and the oily phase are mixed.

The cosmetic composition thus prepared may have effects of improving stabilization of the dosage form and enhancing the texture in use because the cosmetic composition maximizes the effective function of kojyl methylenedioxycinnamate and prevents crystallization from occurring even after prepared into a dosage form.

MODE FOR INVENTION

Hereinafter, the cosmetic composition having high dosage form stability according to the present invention will be described in further detail with reference to examples of the present invention. However, it will be apparent that the present invention is not limited to the examples below.

Experimental Example 1: Precipitation Test Depending on Types of Stabilizers (1) Preparation of Emulsion Composition for Skin Care Emulsions for skin care were prepared using the compositions presented in the following Table 1. First, components 1 to 4 were mixed, and dissolved at 70° C. to prepare an aqueous phase. Thereafter, components 5 to 11 were dissolved at 70° C. to prepare an oily phase. Subsequently, the oily phase was added to the aqueous phase, and primarily emulsified while stirring using a homomixer. Then, component 12 was added thereto to increase a viscosity of the mixture. Finally, bubbles were removed, components 13 and 14 were added thereto, and the resulting mixture was then cooled to prepare an emulsion composition. In this case, SurfMellow BBG (manufactured by Toyobo Co., Ltd.) was used as the MEL.

TABLE 1

| Components (% by weight) | | Example 1 | Comparative Example 1 | Comparative Example 2 | Comparative Example 3 | Comparative Example 4 | Comparative Example 5 |
|---|---|---|---|---|---|---|---|
| Aqueous phase | 1. Purified water | Up to 100 | Up to 100 | Up to 100 | Up to 100 | Up to 100 | Up to 100 |
| | 2. Glycerin | 8 | 8 | 8 | 8 | 8 | 8 |
| | 3. Butylene glycol | 4 | 4 | 4 | 4 | 4 | 4 |
| | 4. Carbomer | 0.1 | 0.1 | 0.1 | 0.1 | 0.1 | 0.1 |
| Oily phase | 5. Caprylic/capric triglyceride | 8 | 8 | 8 | 8 | 8 | 8 |
| | 6. Hydrogenated polydecene | 5 | 5 | 5 | 5 | 5 | 5 |
| | 7. Cetearyl glucoside | 1.5 | 1.5 | 1.5 | 1.5 | 1.5 | 1.5 |
| | 8. Sorbitan stearate | 0.4 | 0.4 | 0.4 | 0.4 | 0.4 | 0.4 |
| | 9. Cetearyl alcohol | 1 | 1 | 1 | 1 | 1 | 1 |
| | 10. Preservative | Proper amount | Proper amount | Proper amount | Proper amount | Proper amount | Proper amount |
| | 11. Fragrance | Proper amount | Proper amount | Proper amount | Proper amount | Proper amount | Proper amount |
| | 12. Triethanolamine | 0.1 | 0.1 | 0.1 | 0.1 | 0.1 | 0.1 |
| | 13. Kojyl methylenedioxycinnamate | 0.1 | 0.1 | 0.1 | 0.1 | 0.1 | 0.1 |
| 14. Stabilizer | MEL | 1 | 0 | 0 | 0 | 0 | 0 |
| | ethyl alcohol | 0 | 0 | 1 | 0 | 0 | 0 |
| | polysorbate 20 | 0 | 0 | 0 | 1 | 0 | 0 |
| | diethoxyethyl succinate | 0 | 0 | 0 | 0 | 1 | 0 |
| | glyceryl/polyglyceryl-6 isostearate/behenate ester | 0 | 0 | 0 | 0 | 0 | 1 |

(2) Precipitation Test

Immediately after the preparation and on weeks 3 and on weeks 10, the emulsion compositions prepared in the example and comparative examples were observed using an optical microscope (×500) and a polarizing microscope (×500) according to the following criteria in order to determine whether crystals were formed. The results are listed in the following Table 2.

<Criteria for Evaluation>
X: No crystals are observed
▲: Crystals with a fine size are observed
○: Crystals are observed
◉: Crystals with a large size are observed

TABLE 2

| | Example 1 | Comparative Example 1 | Comparative Example 2 | Comparative Example 3 | Comparative Example 4 | Comparative Example 5 |
|---|---|---|---|---|---|---|
| Immediately after preparation | X | X | X | X | X | X |
| Week 3 | X | ○ | ○ | ▲ | ▲ | ○ |
| Week 10 | X | ◉ | ◉ | ○ | ○ | ◉ |

Referring to Table 2, a crystal precipitation phenomenon occurred on week 3 in all the emulsion compositions other than the emulsion composition of Example 1 including the MEL.

Particularly, it was confirmed that the crystals were clearly observed on week 3 in the compositions of Comparative Examples 1, 3 and 5, and the crystals were slightly observed on week 3 but clearly observed on week 10 in the compositions of Comparative Examples 3 and 4, indicating that the compositions were not stabilized.

It can be seen that the results were determined by observing the compositions under the optical microscope and the polarizing microscope. The results are shown in FIGS. 1 and 2.

FIGS. 1 and 2 show the results of checking formation of crystals and observing the size of the crystals for the respective compositions immediately after the preparation and on weeks 3 and on weeks 10 using an optical microscope (×500) and a polarizing microscope (×500).

Referring to FIG. 1, it can be seen that the crystals were not formed immediately after the preparation of the composition of Comparative Example 1 including no MEL, but the crystals were observed after 3 weeks of the preparation and the size of the crystals increased after 10 weeks of the preparation.

On the other hand, it can be seen that the composition of Example 1 shown in FIG. 2 was maintained in a stable state without forming the crystals even after 10 weeks of the preparation because the MEL was used in the composition.

Experimental Example 2: Precipitation Test Depending on Content of MEL

To check the optimal content of the MEL used as the stabilizer, emulsion compositions were prepared in the same manner as in the composition of Example 1, and precipitation tests were performed on the emulsion compositions. In this case, the content of the component was adjusted to 100% by weight by varying the content of purified water.

TABLE 3

| | Items | No. 1 | No. 2 | No. 3 | No. 4 | No. 5 | No. 6 | No. 7 |
|---|---|---|---|---|---|---|---|---|
| Components (% by weight) | Kojyl methylenedioxycinnamate | 0.1 | 0.1 | 0.1 | 0.1 | 0.1 | 0.1 | 0.1 |
| | MEL | 0 | 0.25 | 0.5 | 0.75 | 1 | 1.25 | 1.5 |
| Precipitation test | Immediately after preparation | X | X | X | X | X | X | X |
| | Week 3 | ○ | X | X | X | X | X | X |
| | Week 10 | ⊙ | ▲ | X | X | X | X | X |

Referring to Table 3, it can be seen that the crystallization of the kojyl methylenedioxycinnamate was inhibited only when the MEL was added at a content of 0.25% by weight or more, based on the total weight of the cosmetic composition. Particularly, it can be seen that the dosage form stability was maintained after 10 weeks of the preparation only when the MEL was added at a content of 0.5% by weight or more.

Such a content of the MEL means a content of the MEL, when the content of the kojyl methylenedioxycinnamate is 0.1% by weight. As a subsequent test, a test was performed on the content ratios of the MEL and kojyl methylenedioxycinnamate.

Experimental Example 3: Precipitation Test Depending on Content Ratios of Kojyl Methylenedioxycinnamate and MEL To check whether the crystallization occurred according to the content ratios of the kojyl methylenedioxycinnamate and MEL, emulsion compositions were prepared in the same manner as in the composition of Example 1, and precipitation tests were performed on the emulsion compositions. In this case, the content of the component was adjusted to 100% by weight by varying the content of purified water.

TABLE 4

| | Items | No. 8 | No. 9 | No. 10 | No. 11 | No. 12 | No. 13 |
|---|---|---|---|---|---|---|---|
| Components (% by weight) | Kojyl methylenedioxycinnamate | 0.1 | 0.05 | 0.1 | 0.15 | 0.2 | 0.25 |
| | MEL | 0 | 0.5 | 0.5 | 0.5 | 0.5 | 0.5 |
| | Content ratio | — | 1:10 | 1:5 | 1:3.3 | 1:2.5 | 1:2 |
| Precipitation test | Immediately after preparation | X | X | X | X | X | X |
| | Week 3 | X | X | X | X | X | X |
| | Week 10 | X | X | X | X | ▲ | ▲ |

Referring to Table 4, it was confirmed that, when the MEL was added, the crystallization did not occur on week 3, and the crystals were observed in the tests performed on the compositions (Nos. 12 and 13) after 10 weeks of the preparation.

From these results, it can be seen that the crystallization was inhibited even when the MEL and the kojyl methylenedioxycinnamate were added so that the content of the MEL was at least 2.5-fold greater than the kojyl methylenedioxycinnamate.

Experimental Example 4: Precipitation Test Depending on Temperatures of Kojyl Methylenedioxycinnamate and MEL To check the stability of the emulsion compositions according to the temperatures of the kojyl methylenedioxycinnamate and MEL, the formation of crystals according to the temperature and time was determined using the emulsion compositions prepared in Example 1 and Comparative Example 1.

TABLE 5

| Item | | Room temperature | 4° C. | 30° C. | 45° C. |
|---|---|---|---|---|---|
| Comparative | Week 3 | ○ | ◎ | ○ | ○ |
| Example 1 | Week 10 | ◎ | ◎ | ◎ | ◎ |
| Example 1 | Week 3 | X | X | X | X |
| | Week 10 | X | X | X | X |

Referring to Table 5, it was confirmed that the crystallization did not occur even at low and high temperatures (including room temperature) in the case of the composition of Example 1, and this phenomenon lasted after 10 weeks of the preparation, indicating that the composition of Example 1 had high dosage form stability.

On the other hand, it can be seen that the crystallization occurred even at room temperature because the MEL was not used in the composition of Comparative Example 1, and the precipitation at low temperature was accelerated because this phenomenon occurred more seriously at low temperature.

The invention claimed is:

1. Method for inhibiting crystallization and crystal precipitation of kojyl methylenedioxycinnamate represented by the following Formula 1 as an active ingredient in a cosmetic composition for up to 10 weeks, comprising the step of adding a mannosylerythritol lipid (MEL) represented by the following Formula 2 to the cosmetic composition,
wherein the mannosylerythritol lipid acts as a stabilizer for the kojyl methylenedioxycinnamate of Formula 1 in the cosmetic composition,
wherein the kojyl methylenedioxycinnamate is included at a content of 0.05 to 0.25% by weight, based on the total weight of the cosmetic composition,
wherein the mannosylerythritol lipid is included at a content of 0.25 to 5.0% by weight, based on the total weight of the cosmetic composition,
wherein the kojyl methylenedioxycinnamate and the mannosylerythritol lipid are included at a weight ratio of 1:3.3 to 1:10:

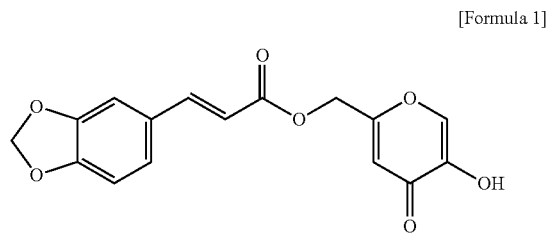 [SMILES: O=C(/C=C/c1ccc2c(c1)OCO2)OCc1cc(=O)c(O)co1]

[Formula 1]

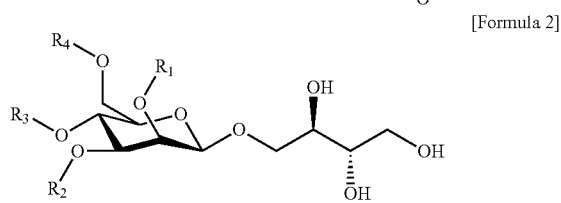

[Formula 2]

wherein $R_1$ and $R_2$ are the same or different from each other, and each independently a C2 to C24 aliphatic acyl group, and
$R_3$ and $R_4$ are the same or different from each other, and each independently an acetyl group or hydrogen.

2. The method of claim 1, wherein $R_1$ and $R_2$ in Formula 2 are the same or different from each other, and each independently an aliphatic acyl group ($3 \leq n \leq 15$) represented by $-C(=O)-(CH_2)_n-CH_3$.

3. The method of claim 1, wherein the mannosylerythritol lipid is represented by the following Formula 3:

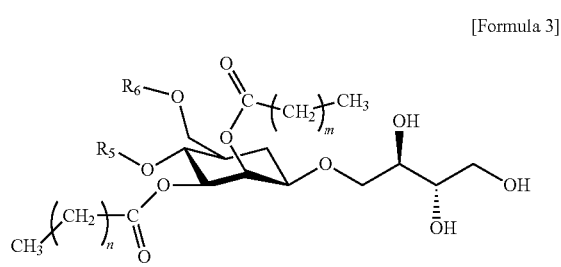

[Formula 3]

wherein $R_5$ and $R_6$ are the same or different from each other, and are an acetyl group or hydrogen, and n or m is an integer ranging from 6 to 10.

* * * * *